(12) United States Patent
Tibbe et al.

(10) Patent No.: US 8,110,101 B2
(45) Date of Patent: *Feb. 7, 2012

(54) METHOD AND APPARATUS FOR IMAGING TARGET COMPONENTS IN A BIOLOGICAL SAMPLE USING PERMANENT MAGNETS

(75) Inventors: Arjan G. J. Tibbe, Deventer (NL); Leon W. M. M. Terstappen, Huntingdon Valley, PA (US)

(73) Assignee: Veridex, LLC, Raritan, NJ (US)

( * ) Notice: Subject to any disclaimer, the term of this patent is extended or adjusted under 35 U.S.C. 154(b) by 152 days.

This patent is subject to a terminal disclaimer.

(21) Appl. No.: 11/897,471

(22) Filed: Aug. 30, 2007

(65) Prior Publication Data

US 2009/0061476 A1 Mar. 5, 2009

(51) Int. Cl.
*B03C 1/02* (2006.01)
*B03C 1/30* (2006.01)
*G01N 33/48* (2006.01)

(52) U.S. Cl. ............. 210/222; 209/39; 436/63; 435/7.2; 435/7.21

(58) Field of Classification Search .................. None
See application file for complete search history.

(56) References Cited

U.S. PATENT DOCUMENTS

| | | | |
|---|---|---|---|
| 4,465,377 A | | 8/1984 | DeBruyne |
| 5,374,531 A | * | 12/1994 | Jensen .......................... 435/7.24 |
| 6,365,362 B1 | | 4/2002 | Terstappen |
| 6,409,925 B1 | * | 6/2002 | Gombinsky et al. .......... 210/695 |
| 6,500,549 B1 | * | 12/2002 | Deppisch et al. .......... 428/425.5 |
| 6,551,843 B1 | | 4/2003 | Rao |
| 6,620,627 B1 | | 9/2003 | Liberti et al. |
| 6,623,982 B1 | | 9/2003 | Liberti et al. |
| 6,645,731 B2 | | 11/2003 | Terstappen et al. |
| 6,861,259 B2 | | 3/2005 | Columbus |
| 7,011,794 B2 | | 3/2006 | Kagan et al. |
| 7,777,885 B2 | | 8/2010 | Coumans |
| 7,828,968 B2 | | 11/2010 | Tibbe et al. |

FOREIGN PATENT DOCUMENTS

| | | |
|---|---|---|
| GB | 2123706 A | 2/1984 |
| WO | WO02077604 | 10/2002 |
| WO | WO03018757 | 3/2003 |
| WO | WO03019141 | 3/2003 |
| WO | WO03065042 | 8/2003 |
| WO | WO03069421 | 8/2003 |
| WO | WO2006102233 | 9/2006 |

* cited by examiner

*Primary Examiner* — Rebecca Prouty
*Assistant Examiner* — Paul Martin
(74) *Attorney, Agent, or Firm* — Ruby T. Hope

(57) ABSTRACT

A system for enumeration of cells in fluids by image cytometry is described for assessment of target populations such as leukocyte subsets in different bodily fluids or bacterial contamination in environmental samples, food products and bodily fluids. Briefly, all cells in a biological sample are fluorescently labeled, but only the target cells are also magnetically labeled. A small, permanent magnet is inserted directly into the chamber containing the labeled sample. The magnets are coated with PDMS silicone rubber to provide a smooth and even surface which allows imaging on a single focal plane. The cells are illuminated and the images of the fluorescent light emitted by the target cells are captured by a CCD camera. Image analysis performed with a novel algorithm provides a count of the cells on the surface that can be related to the target cell concentration of the original sample.

4 Claims, 4 Drawing Sheets

METHOD AND APPARATUS FOR IMAGING TARGET COMPONENTS IN A BIOLOGICAL SAMPLE USING PERMANENT MAGNETS

BACKGROUND

1. Field of the Invention

The invention relates generally to imaging target components in a biological sample. More specifically, methods and apparatus are described that provide for the positive selection of target cells in a blood sample. Small permanent magnets are added directly to a blood sample containing CD4 immuno-magnetic labeled fluorescently stained AO whole blood.

2. Background Art

The use of immunomagnetic separation technology provides greater sensitivity and specificity in the detection of target entities in blood for example, but not limited to, intact circulating cancer cells and endothelial cells. This simple and sensitive diagnostic tool, as described (U.S. Pat Nos. 6,365,362; 6,551,843; 6,623,982; 6,620,627; 6,645,731; WO 02/077604; W003/065042; and WO 03/019141, all incorporated by reference) can be used in the present invention to correlate the statistical survivability of an individual patient based on a threshold level.

A prior diagnostic tool incorporates a blood sample from a cancer patient (WO 03/018757) incubated with magnetic beads, coated with antibodies directed against an epithelial cell surface antigen as for example EpCAM. After labeling with anti-EpCAM-coated magnetic nanoparticles, the magnetically labeled cells are then isolated using a magnetic separator. The immunomagnetically enriched fraction is further processed for downstream immunocytochemical analysis or image cytometry, for example, in the CELLSPOTTER® System (Immunicon Corp., PA), a fluorescent cell imaging system. The magnetic fraction can also be used for downstream immunocytochemical analysis, RT-PCR, PCR, FISH, flowcytometry, or other types of image cytometry.

The CELLSPOTTER® System (Immunicon Corp., PA), a fluorescent cell imaging system, utilizes immunomagnetic selection and separation to highly enrich and concentrate any epithelial cells present in whole blood samples. The captured cells are detectably labeled with a leukocyte specific marker and with one or more tumor cell specific fluorescent monoclonal antibodies to allow identification and enumeration of the captured CTC's as well as unequivocal instrumental or visual differentiation from contaminating non-target cells. At an extraordinary sensitivity of 1 or 2 epithelial cells per 7.5-30 ml of blood, this assay allows tumor cell detection even in the early stages of low tumor mass.

EASYCOUNT™ system (PCT/US03/04468) is a fluorescent imaging system, designed to make a distinction between lymphocytes, granulocytes and monocytes. The system includes a compact electronic optical instruments, analytical methods, image acquisition, and data reduction algorithms for the detection and enumeration of magnetically labeled target cells or particles. Using whole blood as an example, blood cells are fluorescently labeled using one or more target specific fluorescent dyes, such as a DNA staining dye. The cells of interest or target cells in the blood sample are labeled by incubation with monoclonal antibodies conjugated to ferromagnetic particles. The sample is then placed into an appropriate optical detection chamber or covet, which in turn is placed into a magnetic field gradient that selectively causes the magnetically labeled cells to move towards the planar viewing surface of the chamber. The target cells are collected and immobilized substantially uniformly on the optically transparent surface of the chamber. A segment of this surface and the labeled target cells thereon are illuminated by means of one or more LED (light emitting diodes). Subsequently, the light emitted by individual target cells is captured by a CCD (charge coupled device). Image acquisition methods, processing methods, and algorithms, disclosed herein, are used to count the number of captured light-emitting cells and to relate the data output to the target cells per microliter of the analysis sample in the chamber and ultimately to the original specimen.

Currently available methods do not provide a rapid, low cost and consistently reliable means for assessing a target population of cells by flow or image cytometry. Thus, there is a clear need for quick and accurate detection of target components in blood such as cancer or endothelial cells.

SUMMARY OF THE INVENTION

The present invention is a method and means for positive selecting and imaging target entities. This includes a coated permanent magnetic device for magnetic manipulation in the system of the present invention. The system immunomagnetically concentrates the target entity, fluorescently labels, identifies and quantifies target cells by positive enumeration. Subsequent statistical analysis enables the clinician to obtain potential diagnostic information.

More specifically, the present invention provides the apparatus, methods, and kits for diagnosing disease disorders after immunomagnetic imaging. After obtaining a whole blood sample from a patient, a small permanent magnet is added to the whole blood sample. Unlike previously described MAGNEST® (Immunicon Corp., PA), a magnetic cell presentation device for image analysis, configuration, a small NdFeB magnet is directly added to a sample container, for example the CELLSPOTTER® cartridge (Immunicon Corp., PA), a component in the fluorescent cell imaging system U.S. Pat. No. 7,011,794, with 100 ul of CD4 immunomagnetically labeled and fluorescently stained AO whole blood. After 10 minutes the small permanent magnet is pulled out of the sample using an iron rod or another magnet. The magnet is positioned within the container to allow for image analysis.

DETAILED DESCRIPTION OF THE INVENTION

Immunomagnetic isolation, enrichment, and analysis in blood combines immunomagnetic enrichment technology and immunofluorescent labeling technology with an appropriate analytical platform after initial blood draw. The associated test has the sensitivity and specificity to detect rare cells in a sample of whole blood with the utility to investigate their role in the clinical course of the disease such as malignant tumors of epithelial origin.

With this type of technology, circulating tumor cells (CTC) have been shown to exist in the blood in detectable amounts Image cytometric analysis such that the immunomagnetically enriched sample is analyzed by the Cell Spotter® System utilizes a fluorescence-based microscope image analysis system, which in contrast with flowcytometric analysis permits the visualization of events and the assessment of morphologic features to further identify objects (U.S. patent application Ser. No. 11/701,765).

The CELLSPOTTER™ System (Immunicon Corp., PA) refers to an automated fluorescence microscopic system for automated enumeration of isolated cells from blood. The system contains an integrated computer controlled fluorescence microscope and automated stage with a magnetic yoke assembly that will hold a disposable sample cartridge. The magnetic yoke is designed to enable ferrofluid-labeled candidate tumor cells within the sample chamber to be magnetically localized to the upper viewing surface of the sample cartridge for microscopic viewing. Software presents target cells, labeled with antibodies to cytokeratin and having epithelial origin, to the operator for final selection.

Isolation of target cells can be accomplished by any means known in the art. After magnetic separation, the cells bound to the immunomagnetic-linked antibodies are magnetically held at the wall of the tube. Unbound sample is then aspirated and an isotonic solution is added to resuspend the sample. A nucleic acid dye, monoclonal antibodies to cytokeratin (a marker of epithelial cells) and CD 45 (a broad-spectrum leukocyte marker) are incubated with the sample. After magnetic separation, the unbound fraction is again aspirated and the bound and labeled cells are resuspended in 0.2 ml of an isotonic solution. The sample is suspended in a cell presentation chamber and placed in a magnetic device whose field orients the magnetically labeled cells for fluorescence microscopic examination. Cells are identified automatically and candidate target entities presented to the operator for checklist enumeration. An enumeration checklist consists of predetermined morphologic criteria constituting a complete cell.

Figure 1:
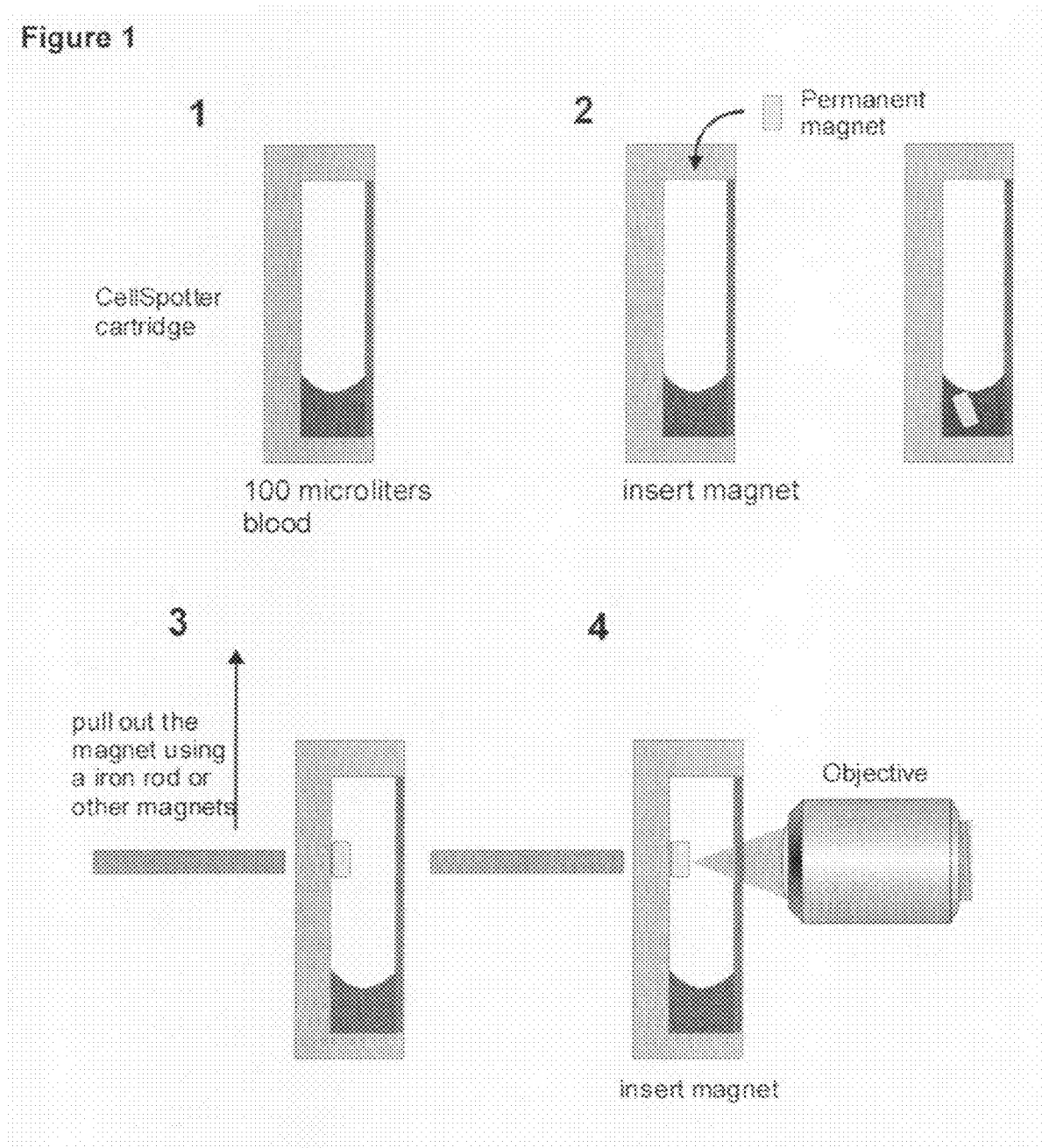
FIG. 1: Steps in the immunomagnetic imaging of target cells using the CELLSPOTTER® cartridge (Immunicon Corp., PA), a component in the fluorescent cell imaging system as the imaging container.

The present invention utilizes a small magnet added directly to the immunomagnetically labeled target entity in a blood sample. The target is further labeled with imaging nucleic acid dyes, cell membrane, and/or cytoskeletal immunofluorescent labels. For example, FIG. 1 depicts a method for imaging CD4 expressing target cells in a whole blood sample. A small neodymium (NdFeB) permanent magnet is added to a whole blood sample after immunomagnetically labeled and fluorescently labeled for CD4. After 10 minutes, the small permanent magnet is separated from the fluid sample and within the sample container to be viewed through a viewing surface.

Figure 2:
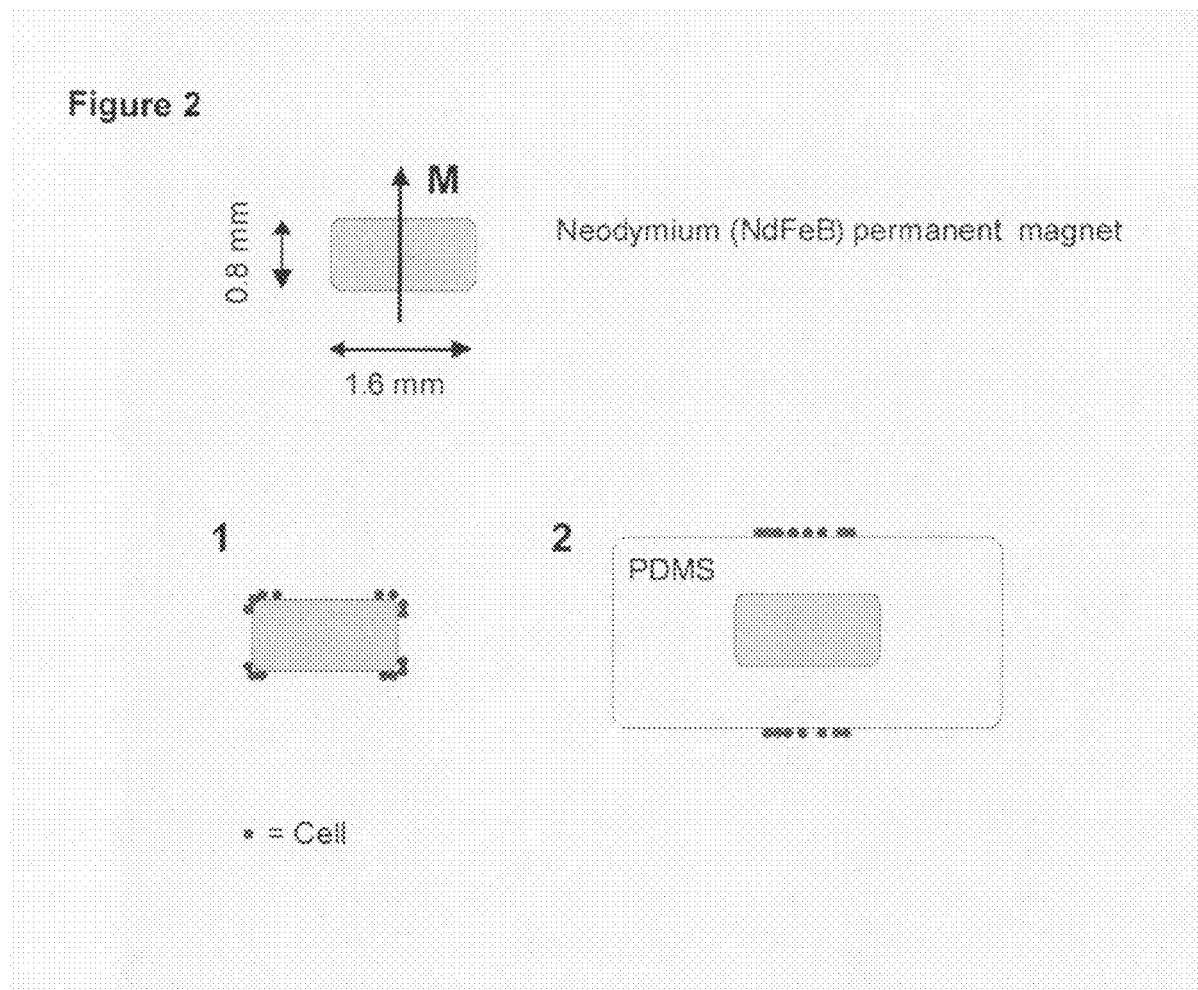
FIG. 2: Schematic representation of one embodiment of the small magnet (M). Panel 1 shows the target entity (cells). Panel 2 shows the target entity oriented on the PDMS silicone rubber coated magnet.
Figure 3:
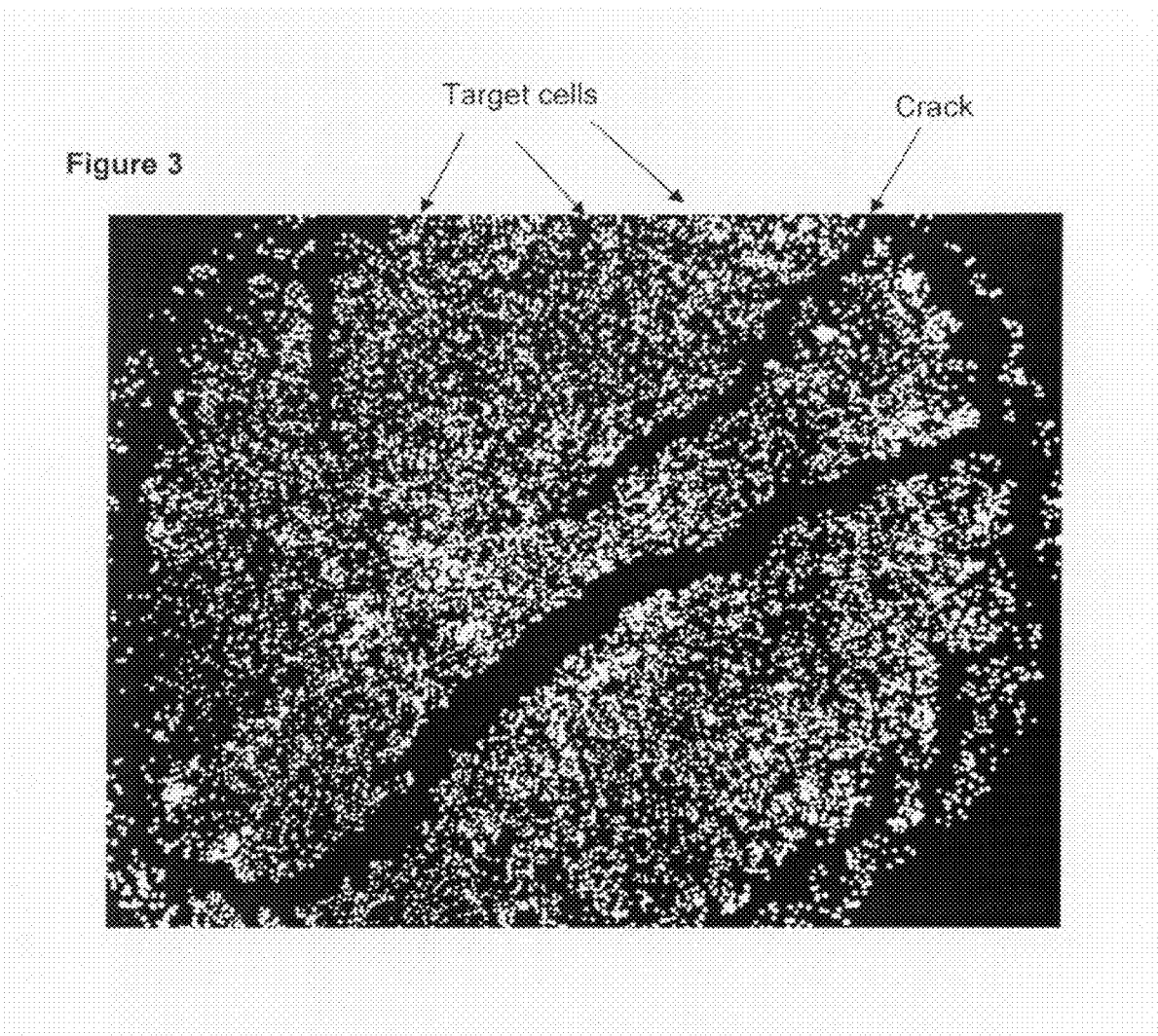
FIG. 3: Image of target entity cells after attachment to magnets without PDMS silicone rubber coating.
Figure 4:
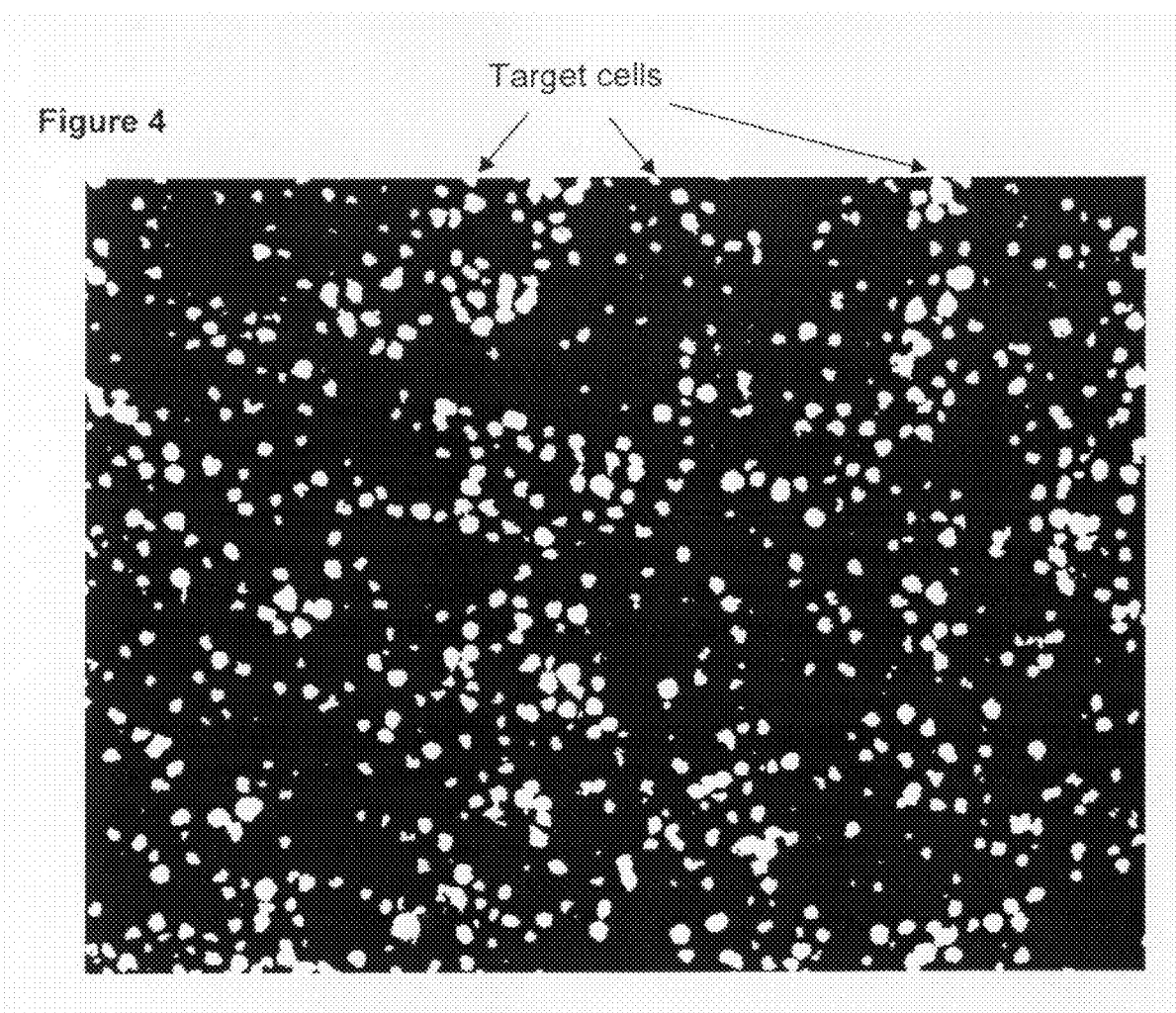
FIG. 4: Image of target entity cells after attachment to magnets coated with PDMS silicone rubber coating.

In one embodiment, the magnet is a disc with a diameter of 1.6 mm and a height of 0.8 mm (see FIG. 2). The smaller magnets are more preferred for this invention. Using this magnet, the target entity (cells) attach to only the magnets as shown in FIG. 3. The cells are not in a single focal plane and quality images are difficult to obtain. The same method, but using encapsulated magnets with PDMS silicone rubber is shown in FIG. 4. Here, the cells attache nicely along a single focal plane. The layer of PDMS on the top of the magnet is approximately 1 mm. The width of the PDMS is approximately 3 mm. Both examples in FIG. 3 and FIG. 4 are images obtained using a 10× objective. The target entities (cells) are presented in a circle with a diameter of approximately 800 um. The "cracks" shown resulted when the magnet was out of the blood sample and dried.

Accordingly in the present invention, the apparatus, method, and kits are provided for the rapid enumeration and characterization of target cells, either epithelial or endothelial in origin, into the blood for prognostic assessment, such as for example survival potential.

What is claimed is:

1. A method for detecting and enumerating a target cell population within a biological specimen said method comprising:
    a. obtaining said biological specimen from a subject;
    b. labeling said target population with colloidal magnetic nanoparticles coupled to a ligand specific for said cell population within said biological specimen wherein said nanoparticles are BSA coated and approximately 0.2 microns in diameter;
    c. isolating said labeled target population wherein said isolating includes art addition of a small PDMS (polydimethylsiloxane)-coated permanent magnet directly in said specimen;
    d. removing said magnet from said specimen;
    e. acquiring an image of said labeled target population wherein said target population is attached to said magnet along a single focal plane, and
    f. analyzing said image to detect and enumerate said labeled target population.

2. The method of claim 1 wherein said target population is CD4 expressing cells.

3. The method of claim 1 wherein said magnet is neodymium.

4. The method of claim 1 wherein said magnet is a disc having a diameter of about 1.6 mm and a height of 0.8 mm.

* * * * *